(12) United States Patent
Stephanopoulos et al.

(10) Patent No.: US 7,603,239 B2
(45) Date of Patent: Oct. 13, 2009

(54) METHODS AND SYSTEMS FOR GENERATING PEPTIDES

(75) Inventors: Gregory Stephanopoulos, Winchester, MA (US); Christopher R. Loose, Cambridge, MA (US); Kyle Jensen, Berkeley, CA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 11/123,399

(22) Filed: May 5, 2005

(65) Prior Publication Data
US 2006/0035281 A1    Feb. 16, 2006

Related U.S. Application Data

(60) Provisional application No. 60/568,570, filed on May 5, 2004.

(51) Int. Cl.
*G06F 19/00*    (2006.01)
(52) U.S. Cl. .......................................................... 702/19
(58) Field of Classification Search ................... 702/19, 702/20
See application file for complete search history.

(56) References Cited

U.S. PATENT DOCUMENTS

| | | | |
|---|---|---|---|
| 4,098,728 A | 7/1978 | Rosenblatt | |
| 4,211,227 A | 7/1980 | Anderson et al. | |
| 4,636,208 A | 1/1987 | Rath | |
| 5,180,375 A | 1/1993 | Feibus | |
| 6,031,074 A | 2/2000 | Saxinger | |
| 6,188,965 B1 | 2/2001 | Mayo et al. | |
| 6,269,312 B1 | 7/2001 | Mayo et al. | |
| 6,642,353 B1 | 11/2003 | McConnel et al. | |
| 6,708,120 B1 | 3/2004 | Mayo et al. | |
| 6,711,879 B2 | 3/2004 | Korteweg et al. | |
| 2003/0130827 A1* | 7/2003 | Bentzien et al. | ............... 703/11 |
| 2004/0043430 A1* | 3/2004 | Dahiyat et al. | ............... 435/7.1 |
| 2008/0133142 A1 | 6/2008 | Rihoutsos et al. | |

FOREIGN PATENT DOCUMENTS

WO    WO 94/25484    11/1994
WO    WO 00/09553    2/2000

OTHER PUBLICATIONS

Looger et al. Nature. May 8, 2003;423(6936):185-90.*

(Continued)

*Primary Examiner*—Michael Borin
(74) *Attorney, Agent, or Firm*—Pabst Patent Group LLP

(57) ABSTRACT

Antimicrobial peptides are small proteins used by the innate immune system to combat bacterial infection in multicellular eukaryotes. There is mounting evidence that these peptides are less susceptible to bacterial resistance than traditional antibiotics and that they may form the basis for a novel class of therapeutics. Systems and methods may treat the amino acid sequences of these peptides as a formal language and build a set of right-linear grammars that describe this language. These grammars may allow for rationally designed novel antimicrobial peptides in silico. These peptides conform to the syntax of natural antimicrobial peptides lack significant homology to any natural sequences, thus populating a previously unexplored region of protein sequence space. Synthesis of these peptides, leads to de novo AmPs.

12 Claims, 4 Drawing Sheets

OTHER PUBLICATIONS

Koehl et al. J. Mol.Biol., 293, 1183-1193, 1999.*

National Library for Medicine, Computational Molecular Modeling In Peptide Drug Design; Int J. Pept Protein Res. Dec. 1994; 44(6):513-31.

Computational Design of an Integrin I Domain Stabilized In the Open High Affinity Conformation, Nature Structural Biology, doi: 10.1038/77978. Aug. 2000. vol. 7, No. 8, pp. 674-678.

Enzyme-like Proteins by Computational Design, by Daniel N. Bolon and Stephen L. Mayo, Proceedings of the National Academy of Sciences of the USA ("PNAS"), Dec. 4, 2001, vol. 98, No. 25, 14274-14279.

A Method For Computational Combinatorial Peptide Design of Inhibitors of Ras Protein, by Jun Zeng and Herbert R. Treutlein, Protein Engineering, vol. 12, No. 6, 457-468, Jun. 1999—Oxford University Press.

Computational Approachs to Structure-based Ligand Design by Diane Joseph-McCarthy—Pharmacology & Therapeutics 84 (1999) 179-191.

Computational Protein Design—Christina M. Kraemer-Pecore, Andrew M. Wollacott and John R. Desjarlais.

Design of Peptides, Proteins, and Peptidomimetics in Chi Space—Biopolymers. 1997;43(3):219-66—National Library of Medicine, PubMed.

Modern Computational Techniques—IBM Systems Journal, vol. 40, No. 2, 2001.

Sequence Analysis and Membrane Partitioning Energies of a-helical antimicrobial peptides, by Xing Han and Wenjun Kang—Bioinformatics, vol. 20, No. 6, 2004, pp. 970-973, D0I:10. 1983/bioinformatics/bth027.

Amino Acid Substitution Matrices From Protein Blocks—Proc. National Academy of Science USA, vol. 89, pp. 10915-10919, Nov. 1992 -Biochemistry.

Combinatorial Pattern Discovery in Biological Sequences: the TEIRESIAS Algorithm—Bioinformatics, vol. 14, No. 1, 1998, pp. 55-67.

Schneider et al., "Peptide design by artificial neural networks and computer-based evolutionary search," Proc. Natl. Acad. Sci., 95(21):12179-12184 (1998).

Altschul, et al., "Basic local alignment search tool", J. Mol. Biol., 215(3):403-10 (1990).

Anonymous, "IUPAC-IUB Commission on Biochemical Nomenclature Symbols for Amino-Acid Derivatives and Peptides. Recommendations", Biochemistry, 11(9):1726-32 (1971).

Bailey and Elkan, "Fitting a mixture model by expectation maximization to discover motifs in biopolymers", Proc. Int. Conf. Intell. Syst. Mol. Biol., 2:28-36 (1994).

Bairoch and Apweiler, "The SWISS-PROT protein sequence database and its supplement TrEMBL in 2000", Nucleic Acids Res., 28(1):45-8 (2000).

Boman, "Antibacterial peptides: basic facts and emerging concepts", J. Intern. Med., 254(3):197-215 (2003).

Chen, et al., "RGD-Tachyplesin inhibits tumor growth", Cancer Res., 61(6):2434-8 (2001).

Chomsky, "Three models for the description of language", IRE Transactions on Information Theory, IT-2(3), 113-124 (1956).

Dahiyat, et al., "De novo protein design: fully automated sequence selection", Science, 278(5335):82-7 (1997).

Devereux, et al., "A comprehensive set of sequence analysis programs for the VAX", Nucleic Acids Res., 12(1 Pt 1):387-95 (1984).

Ellerby, et al., "Anti-cancer activity of targeted pro-apoptotic peptides", Nat. Med., 5(9):1032-8 (1999).

Epand and Vogel, "Diversity of antimicrobial peptides and their mechanisms of action", Biochim. Biophys. Acta., 1462(1-2):11- 28 (1999).

Ge, et al., "In vitro antibacterial properties of pexiganan, an analog of magainin", Antimicrob. Agents Chemother., 43(4):782-8 (1999).

Giangaspero, et al., "Amphipathic alpha helical antimicrobial peptides", Eur. J. Biochem., 268(21):5589-600 (2001).

Hancock and Patrzykat, "Clinical development of cationic antimicrobial peptides: from natural to novel antibiotics", Curr. Drug Targets Infect. Disord., 2(1):79-83 (2002).

Kamtekar, et al., "Protein design by binary patterning of polar and nonpolar amino acids", Science, 262(5140):1680-1685 (1993).

Kim, et al., "In vitro activities of native and designed peptide antibiotics against drug sensitive and resistant tumor cell lines", Peptides, 24(7):945-53 (2003).

Kimbrell and Beutler, "The evolution and genetics of innate immunity", Nat. Rev. Genet., 2(4):256-667 (2001).

Kopple, "Peptides and Amino Acids", W. A. Benjamin Inc., pp. 2 and 33, Paub: New York and Amsterdam, 1966.

Lawrence, et al., "Detecting subtle sequence signals: a Gibbs sampling strategy for multiple alignment", Science, 262(5131):208-14 (1993).

Maizel and Lenk, "Enhanced graphic matrix analysis of nucleic acid and protein sequences", Proc. Natl. Acad. Sci. U.S.A., 78(12):7665-9 (1981).

Moerman, et al., "Antibacterial and antifungal properties of alpha-helical, cationic peptides in the venom of scorpions from southern Africa", Eur. J. Biochem., 269(19):4799-810 (2002).

Putsep, "Deficiency of antibacterial peptides in patients with morbus Kostmann: an observation study", Lancet, 360(9340):1144-9 (2002).

Regan and Degrado, "Characterization of a helical protein designed from first principles", Science, 241(4868):976-8 (1988).

Rice, et al., "EMBOSS: the European Molecular Biology Open Software SuiteEMBOSS: the European Molecular Biology Open Software Suite", Trends Genet., 16(6):276-7 (2000).

Rigoutsos, et al., "Dictionary building via unsupervised hierarchical motif discovery in the sequence space of natural proteins", Proteins, 37(2):264-77 (1999).

Rigoutsos, "The emergence of pattern discovery techniques in computational biology", Metab. Eng., 2(3):159-77 (2000).

Rolff and Siva-Jothy, "Invertebrate ecological immunology", Science, 301(5632):472-5 (2003).

Salzman, et al., "Protection against enteric salmonellosis in transgenic mice expressing a human intestinal defensin", Nature, 422(6931):522-6 (2003).

Schittek, et al., "Dermcidin: a novel human antibiotic peptide secreted by sweat glands", Nat. Immunol., 2(12):1133-7 (2001).

Searls, "Artificial intelligence and molecular biology", (L. Hunter, ed.), pp. 47-120, AAAI Press, 1992.

Searls, "The language of genes", Nature, 420(6912):211-7 (2002).

Simmaco, et al., "Antimicrobial peptides from amphibian skin: what do they tell us?", Biopolymers, 47(6):435-50 (1998).

Simmaco, et al., "Antimicrobial peptides from skin secretions of Rana esculenta. Molecular cloning of cDNAs encoding esculentin and brevinins and isolation of new active peptides", J. Biol. Chem., 269(16):11956-61 (1994).

Strom, et al., "The pharmacophore of short cationic antibacterial peptides", J. Med. Chem., 46(9):1567-70 (2003).

Tiozzo, et al., "Wide-spectrum antibiotic activity of synthetic, amphipathic peptides", Biochem. Biophys. Res. Commun., 249(1):202-6 (1998).

Tossi and Sandri, "Molecular diversity in gene-encoded, cationic antimicrobial polypeptides", Curr. Pharm. Des., 8(9):743-61 (2002).

Tossi, et al., "Amphipathic, alpha-helical antimicrobial peptides", Biopolymers, 55(1):4-30 (2000).

Wang and Wang, "APD: the Antimicrobial Peptide Database", Nucleic Acids Res., 32(Database issue):D590-2 (2004).

Wilson, et al., "Regulation of intestinal alpha-defensin activation by the metalloproteinase matrilysin in innate host defense", Science, 286(5437):113-7 (1999).

Zhang, et al., "Contribution of human alpha-defensin 1, 2, and 3 to the anti-HIV-1 activity of CD8 antiviral factor", Science, 298(5595):995-1000 (2002).

Brazma, et al., "Pattern discovery in biosequence", Lecture Notes in Computer Science, 1433:257-270. Springer Berlin Heidelberg, 1998.

* cited by examiner grammar 1: T[L/G][T/I/P] L L[T/I/S/P][A/T] L L[L/G]  (SEQ ID NO: 11)

query: MKSTGPLLSALLLAVTAGGDP ⟶ S=16/21
(SEQ ID NO: 12)

grammar 2: [A/F/T]L[I/L] L A[I/V][S/F/A/T][V/A][G/A/D][P/G/S/Q]  (SEQ ID NO: 13)

METHODS AND SYSTEMS FOR GENERATING PEPTIDES

RELATED APPLICATIONS

This application claims priority to U.S. Provisional Application U.S. Ser. No. 60/568,570 filed on May 5, 2004, entitled Systems and Methods for Generating Peptides, and naming Gregory Stephanopoulos as inventor, the contents of which are incorporated by reference.

BACKGROUND

Recently, advances have been made in synthesizing stable proteins with novel sequences. Efforts to design proteins rely largely on knowledge of the physical properties that determine protein structure, such as the patterns of hydrophobic and hydrophilic residues in the sequence, salt bridges and hydrogen bonds, and secondary structural preferences of amino acids. Various approaches to apply these principles have been attempted. For example, helical proteins were generated and discussed in Regan, et al., Science 241:976-978 (1988) and an experimental method was developed using random mutagenesis and described in Kamtekar, et al., Science 262:1680-1685 (1993). Similarly, U.S. Pat. No. 6,708,120 discusses a method that starts with a protein backbone structure and then modifies the backbone structure by establishing a group of potential rotamers for each of the variable residue positions in the backbone. The process then quantitatively analyzes and evaluates the interaction of each of the potential rotamers with all or part of the remainder of the protein backbone. Through this process, the method attempts to generate a set of optimized protein sequences. Additionally, de novo protein design has been discussed that proposes fully automated sequence selection. Dahiyat, B. I., and Mayo, S. L., De novo Protein Design: Fully Automated Sequence Selection. Science, 278, 82 (1997). This work demonstrated a computational design algorithm based on physical-chemical potential functions and stereochemical constraints. The constraints were used to screen a combinatorial library of possible amino acid sequences for compatibility with a design target. Through this algorithm, non-wild type proteins were designed, as confirmed by BLAST searches, that had a compact well-ordered structure, in agreement with the design target.

Although these approaches have brought some clarity and discipline to the process of peptide design, the standard approach today is still to synthesize new peptides by creating synthesized peptides that look very similar to a known peptide having a particular function or purpose. The hope is that the synthesized peptide will have similar functionality as the naturally occurring peptide, and minimal or no side effects. The standard method is still employed today because synthesizing peptides is relatively simple and the currently developed approaches for computationally determining peptide sequences of interest are difficult to implement and offer only marginal improvement over heuristic sequence selection. Further, the existing processes have been limited in scope in as much as they typically begin from a starting point that is related to or defined by a single protein or peptide of interest. This tends to provide a narrow focus for the later development processes, and keeps newly developed proteins tightly bound to the selected seed sequence.

Thus, there is a need in the art for sequence design processes that provide a more comprehensive and methodical approach to protein design.

SUMMARY

Thus, it is an object of the invention to provide design processes for proteins and other biological molecules that provide improved accuracy of target selection.

It is a further object of the invention to provide such design processes that operate more efficiently and provide improved control over the synthesis process.

The systems and methods described herein include systems and methods for designing peptides that have a desired characteristic or property. For example, the systems and methods described herein may be used to design, among other things peptides and peptide analogs that have antimicrobial properties or certain structural features. In one practice, the methods according to the invention include identifying a database of peptide sequences that are associated with the characteristic of interest. For example, a database of peptides may be identified that contains peptides that have antiviral properties, wound response properties, antimicrobial properties or some other property of interest. Once the database is identified, the database may be processed in a pattern recognition procedure that identifies a set of patterns that could be understood as representative of a peptide having the characteristic of interest.

In one particular practice, the method employs a pattern recognition process that finds a set of grammars that are representative of peptides having the characteristic of interest.

A set of randomly generated peptides sequences may then be processed to score the randomly generated sequences against the identified patterns to correlate the patterns to the sequences and determine a degree of association or a similarity between a respective one of the random sequences and the set of identified patterns.

In one particular practice, the methods described herein employ an evolutionary correlation process that begins with a set of random peptide sequences and reproduces and mutates those sequences according to an evolutionary algorithm and then tests the produced sequences against the set of identified patterns to identify a subset of the produced patterns that correlate sufficiently strongly to the patterns to indicate that the respective sequence likely exhibits the characteristic of interest. In a further optional practice, the evolutionary process may be run iteratively for the purpose of cycling through the mutation, reproduction and selection steps until a set of candidate peptides sequences are generated that are tightly correlated to the patterns earlier identified.

In a further step, the methods may include selecting a subset of the generated highly correlated peptide sequences to operate as templates for creating peptides having sequences that were selected to match the sequences generated in the evolutionary selection process described above. The peptides can be tested to determine the biological presence of the characteristic of interest.

In a further optional process, the systems and methods described herein may be employed to design peptides having two or more characteristics of interest. For example, the methods described herein may be employed to design peptides having a first characteristic, such as being antimicrobial, and a second characteristic such as having an acceptable level of toxicity.

Other objects of the invention will, in part, be obvious, and, in part, be shown from the following description of the systems and methods shown herein.

BRIEF DESCRIPTION OF THE DRAWINGS

The foregoing and other objects and advantages of the invention will be appreciated more fully from the following further description thereof, with reference to the accompanying drawings wherein.

DESCRIPTION OF THE ILLUSTRATED EMBODIMENTS

To provide an overall understanding of the invention, certain illustrative embodiments will now be described. However, it will be understood by one of ordinary skill in the art that the systems and methods described herein can be adapted and modified for other suitable applications and that such other additions and modifications will not depart from the scope hereof. In particular, it will be understood that although the systems and methods described herein are done largely with reference to examples of peptide designs, the invention is not to be so limited and these systems and methods may be applied to the development and design of other biological and non-biological sequences. The modifications and additions appropriate for such applications will in part obvious to those of skill in the art and in part be apparent from the description and examples set out below.

Accordingly, the systems and methods described herein include, among other things, systems and methods for designing peptides that have a desired characteristic or property. For example, the systems and methods described herein can be used to design peptides that have antimicrobial properties. In one practice, the methods include identifying a database of peptide sequences that are associated with the characteristic of interest. For example, a database of peptides may be identified that have antiviral properties, wound response properties, antimicrobial properties or some other property of interest. Once the database is identified, the database may be processed in a pattern recognition procedure that identifies a set of patterns that could be understood as representative of a peptide having the characteristic of interest.

Figure 1:
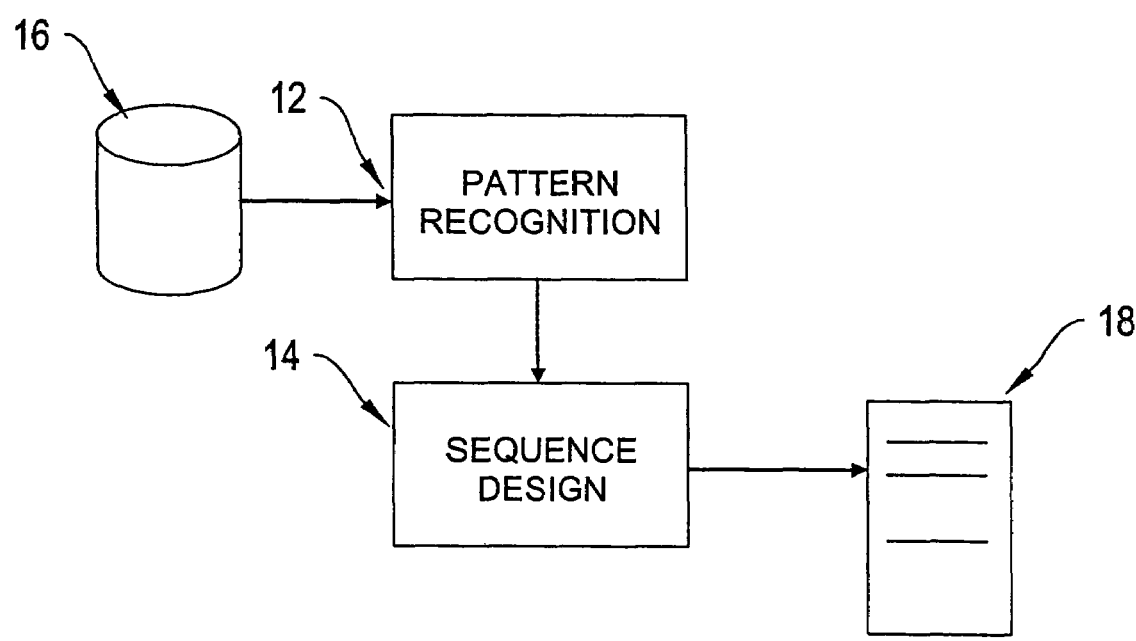
FIG. 1 depicts a functional block diagram representative of a system according to the invention.

The systems and methods described above provide for a comprehensive analysis of the structure that may lead to a desired characteristic behavior. To this end, these systems and methods may process a substantial volume of sequence data, as well as carry out a substantial number of repetitive operations and calculations. As such, automated tools for processing the data are desirable. The systems and methods described herein lend themselves well to automation, at least for portions of the process, and one such automated system is depicted as a functional block diagram in FIG. 1. Specifically, FIG. 1 depicts a system 10 that includes a pattern recognition processor 12, a sequence design processor 14, a database of sequence data 16 and a data file 18 having the designed sequences, such as peptide sequences, thereon. The system 10 depicted in FIG. 1 will typically be implemented as a computer program operating on one or more conventional data processing platforms, such as an IBM PC-compatible computer running the Windows operating systems, or a SUN workstation running a Unix operating system. Alternatively, the data processing system can comprise a dedicated processing system that includes an embedded programmable data processing system. For example, the data processing system can comprise a single board computer system that has been integrated into a system for performing peptide design process. As such, the system 10 may be a dedicated piece of laboratory equipment. However, in either of these cases, the system 10 will be understood as a computer program that directs the operation of a data processing platform to configure the platform into the system 10 depicted in FIG. 1. As such, the invention may also be understood to include computer readable media having stored thereon instructions for operating a data processing system to carry out the functions and operations described herein.

In one embodiment the pattern recognition processor 12 is a software module that executes on the data processing platform to direct the platform to collect sequence data from the database 16, and process that data to recognize patterns that occur within the sequences. An exemplary process using the Teiresias pattern discovery process is described more fully below. The depicted database 16 may be any suitable database system, including the commercially available Microsoft Access database, and may be a local, remote or a distributed database system. The design and development of suitable database systems are described in McGovern et al., A Guide To Sybase and SQL Server, Addison-Wesley (1993). The database 16 may be supported by any suitable persistent data memory, such as a hard disk drive, RAID system, tape drive system, floppy diskette, or any other suitable system. In certain embodiments, the database 16 is substantially remote from the pattern recognition processor 12, and a network connection is employed to provide access to the data stored in the database.

The systems and methods described herein may be employed for designing any type of peptide or protein. For purposes of clarity, the system 10 will now be described with reference to an exemplary process for generating antimicrobial peptides of the type that may be effective as antibiotic therapies. However, it shall be understood by those of skill in the art that this is merely an example of the type of peptide or protein that can be generated according to the invention and that the systems and methods described herein are not so limited that may be employed in other applications. For example, peptides may be employed for treating cancer, diabetes, for industrial applications, such as for antimicrobial agents in paints, peptide toxins for insecticides, or for any other application. Different peptides and applications of such peptides are set forth in the references, which references are cited throughout this disclosure, and are hereby incorporated by reference in their entirety.

In one particular application, the systems and methods described herein have been employed for synthesizing antimicrobial peptides. A peptide as the term is used herein will be understood to encompass organic compounds composed of amino acids, whether natural or synthetic, and linked together chemically by peptide bonds. The peptide bond involves a single covalent link between the α-carboxyl (oxygen-bearing carbon) of one amino acid and the amino nitrogen of a second amino acid. Small peptides with fewer than about ten constituent amino acids are typically called oligopeptides, and peptides with more than ten amino acids are termed polypeptides. Compounds with molecular weights of more than 10,000 (50-100 amino acids) are usually termed proteins. All these compounds may be designed using the systems and methods described herein.

Antimicrobial peptides (AmPs) are small proteins used by the innate immune system to attack and kill bacteria, J. Rolff, M. T. Siva-Jothy, Science 301, 472 (2003), D. A. Kimbrell, B. Beutler, Nat Rev Genet 2, 256 (2001). These peptides are ubiquitous among multicellular eukaryotes and have been found in diverse contexts including frog skin, M. Simmaco, G. Mignogna, D. Barra, Biopolymers 47, 435 (1999), scorpion venom, L. Moerman, et al., European Journal of Biochemistry 269, 4799 (2002), and human sweat, B. Schiettek, et al., Nature Immunology 2, 1133 (2001).

There is mounting evidence that antimicrobial peptides may become effective antibiotic therapies, R. E. W. Hancock, A. Patrzykat, Current Drug Targets-Infectious Disorders 2, 70 (2002). Indeed, many AmPs show activity against pathogens that are resistant to traditional antibiotics such as penicillin, tetracycline, and vancomycin, Y. Ge, et al., Antimicrob Agents Chemother 43, 782 (1999), E. Tiozzo, G. Rocco, A. Tossi, D. Romeo, Biochemical and Biophysical Research Communications 249, 202 (1998), M. B. S. m, et al., Journal of Medicinal Chemistry 46, 1567 (2003). In humans, malfunctioning AmPs can lead to severely immunocompromised phenotypes (10, 11) K. Putsep, G. Carlsson, H. G. Boman, M. Andersson, Lancet 360, 1144 (2002), H. G. Boman, Journal of Internal Medicine 254, 197 (2003). Animal models deficient in AmPs succumb to pathogen challenge, C. L. Wilson, et al., Science 286, 113 (1999), whereas transgenic mice expressing human AmPs exhibit a markedly increased resistance to infection, N. H. Salzman, D. Ghosh, K. M. Huttner, Y. Paterson, C. L. Bevins, Nature 422, 522 (2003). In addition to their antibiotic uses, AmPs may have other interesting clinical applications: for example they are involved in the immune response of long-term HIV nonprogressors, L. Zhang, et al., Science 298, 995 (2002) and may be useful in treating certain cancers, S. Kim, S. S. Kim, Y.-J. Bang, S.-J. Kim, B. J. Lee, Peptides 24, 945 (2003), H. M. Ellerby, et al., Nature Medicine 5, 1032 (1999), Y. Chen, et al., Cancer Research 61, 2434 (2001).

The many disease-relevant behaviors of antimicrobial peptides are understood as a consequence of their ability to broadly distinguish eukaryotic cells from pathogenic invaders. In general, AmPs have a net positive charge and an amphipathic 3-D structure that gives the peptides an electrostatic affinity to the out-leaflet of the microbial membrane, A Giangaspero, L. Sandri, A. Tossi, European Journal of Biochemistry 268, 5589 (2201), R. M. Epand, H. J. Vogel, Biochimica et Biophysica Acta—Biomembrances 1462, 11 (1999).

Returning to FIG. 1, it is noted that there are a number of antimicrobial sequences databases that may be used or accessed to provide the database 16 of sequence data. The database 16 may contain the sequences of gene encoded antimicrobial peptides and proteins. It may also include, when available, the sequences of precursors and of putative antimicrobial peptides as deduced from DNA sequencing. Typically, the available databases are oriented towards peptides of animal and plant sequences. But peptides and proteins of bacterial origin may be included. One database is the AMSDb that is correlated to the SWISS-PROT protein sequences database. That database has recently been updated and maintained within the framework of the European "PANAD" (Peptides As Novel Antiinfective Drugs) Project (European 5th framework programme, project N° QLK2-CT-2000-00411). The database employed will depend upon the specifics of the application. For example, it may be that the system 10 is directed to designing AmPs for plants, and as such the pattern analysis performed by the pattern recognition processor 12 may only process AmPs for plants. As such the database 16 may be limited to AmPs associated only with plants. Additionally, databases may be developed that are directed to AmPs having a particular mechanism of action. For example, AmPs generally disrupt the membranes of a target cell, causing lysis of the cell. How this occurs, may vary and recently, several peptides with unusual folds with strong antimicrobial activity have been identified, and their solution determined by NMR. In certain embodiments and practices, it may be that the pattern recognition process 12 is employed to find a grammar for AmPs having this particular feature. Or alternatively, patterns may be identified that the system uses to eliminate candidate sequences. In either case, the database selected may be chosen by one of the skill in the art such that the data studied and processed is suited to the task.

For example, preliminary studies of AmPs indicate that their amphipathic structure gives rise to a modularity among AmP sequences. The repeated usage of sequence modules— which may be a relic of evolutionary divergence and radiation—may be analogized to the use of words and phrases in a natural language, such as English. For example, the pattern Q.EAG.L.K.K (SEQ ID NO: 1) (the "." means that any amino acid will suffice) is present in over 90% of cecropins, an AmP common in insects.

Based, at least in part, on this observation, the systems and methods described herein model the AmP sequences as a formal language over the set of amino acids, D. Jurafsy, J. H. Martin, Speech and Language Processing: An Introduction to Natural Language Processing, Computational Linguistics, and Speech Recognition (Prentice Hall, Upper Saddle River, New Jersey, 2000).

Furthermore, in certain particular embodiments and practices, this language can be generated by a set of right-linear grammars, such as the ceropin grammar above. Right-linear grammars—also known as regular grammars or regular expressions—are simple rules that describe allowed arrangements of characters, N. Chomsky, IRE Transactions on Information Theory 2, 113 (1956). These grammars are useful for modeling short-range dependencies in primary sequences and are commonly used to represent motifs or patterns, D. B. Searls, Nature 420, 211 (2002), D. B. Searls, Artificial Intelligence and Molecular Biology, L. Hunter, ed. (AAAI Press, 1992), pp 47-120.

To elucidate the grammar of AmPs, a pattern recognition process was employed, such as the Teiresias pattern discovery tool (see, I. Rigoutsos, A. Floratos, Bioinformatics 14, 55 (1998) or a detailed description of the Teiresias algorithm). Given a formal language, Teiresias enumerates right-linear grammars that are maximal in both composition and length. Using Teiresias, the methods described herein discovered what is understood as an exhaustive set of approximately 44 K grammars in the set of known eukaryotic AmP sequences. These sequences consisted of approximately 750 AmPs from AMSdb, A. Tossi, Antimicrobial sequences database (AMSDb) (2002), which were supplemented with about an additional 200 antimicrobial peptides from Swiss-Prot/TrEMBL, A. Bairoch, R. Apweiler, Nucleic Acids Research 28, 45 (2002) that were not included in AMSdb.

Together, the set of ~44 K grammars may be understood to describe the "language of AmP sequences." In the linguistic model employed, a sequence is a string of amino acids and it is "grammatical" if the sequence conforms to one or more grammars, i.e. it matches at least one regular expression. The semantic interpretation of this sentence is the peptide's function: in this case, antimicrobial activity.

To facilitate the design of synthetic AmPs, a heuristic metric S was employed, which is the degree to which a query sequence is grammatical. The metric is generated by a scoring function that gives a measure S that is representative of how closely a query (or candidate) sequence follows the grammar. There are numerous techniques for scoring the similarity between two or more sequences, and any suitable technique may be employed. In one particular practice, a local score is assigned along the backbone of a query sequence, which is equal to the number of grammars, or fractions of grammars with at least 10 amino acids, that are incident upon the length of the query sequence. The total score for the sequence, S, is the fraction of the sequence's length that is covered by grammars.

$S$ = sequence's length covered by grammars/length of sequence.

Figures 2A, 2B:
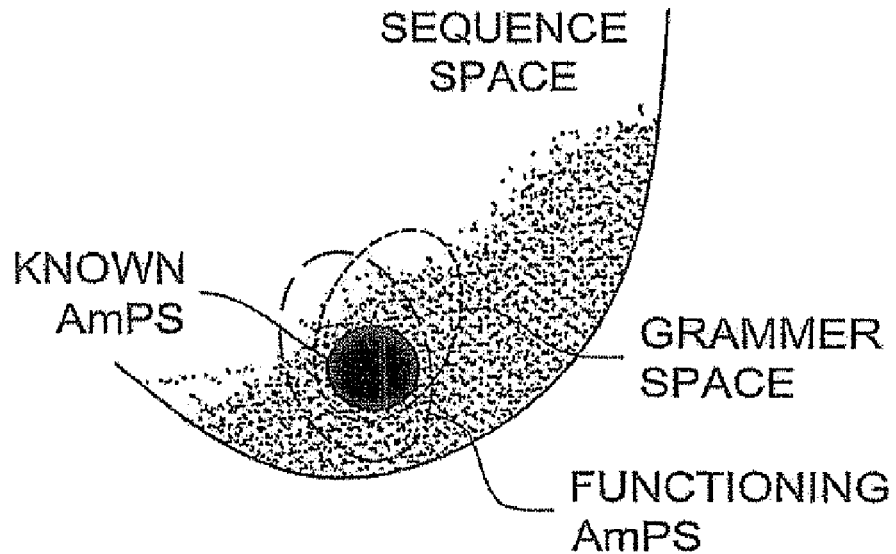
FIGS. 2A and 2B depict an example of a peptide design space and an example of a query sequence scoring process to determine the degree of association between a query string a grammar.

This process is depicted in FIG. 2B. More particularly, FIGS. 2A and 2B depict a peptide design space (FIG. 2A), and an example of a scoring process for generating a measure sequences that comply with the grammar, and a functioning AmP space 26 representative of the portion of the total sequence space that contains a sequence representative of a peptide that has an anti-microbial function. It will be noted that in FIG. 2A, the grammar space 24 and the functioning AmP space 26, are shown to diverge. This represents the understanding that not all sequences that are grammatical will provide a functioning AmP, and similarly, not all functioning AmPs will be grammatical, in that they comply with the grammars determined in this process. Such divergence is possible and likely, although not necessary. The depicted divergence indicates that in one practice, a plurality of candidate AmPs are to be created through the processes described herein, as each candidate AmP may not ultimately have the desired biological activity. FIG. 2A further depicts the sequence space 28 defining the set of naturally occurring peptides that have the characteristic of interest. As will be described below, the peptide design process may optionally filter out from the pool of query sequences, those sequences that are known to occur naturally.

TABLE 1

The synthetic antimicrobial peptides used in this study. For each synthetic AmP we also designed two control sequences (a and b), which have the same amino acid composition as the synthetic peptide but have a S score of zero. The table also shows statistics relavant to AmPs, which were calculated using the EMBOSS software package (34).

| Peptide | S | Size | Charge | p1 | Sequence |
|---|---|---|---|---|---|
| synth-1: | | | | | |
| synth-1 | 1 | 20 | 4.5 | 11.92 | NKVKKFLTGAHRLLFTFLFV (SEQ ID NO:2) |
| synth-1a | 0 | 20 | 4.5 | 11.92 | VVLKLLFFKFNLPHKTRTAG (SEQ ID NO:3) |
| synth-1b | 0 | 20 | 4.5 | 11.92 | LVLTFLFATPKLNGRVKKFH (SEQ ID NO:4) |
| synth-2: | | | | | |
| synth-2 | 1 | 31 | 10.0 | 11.28 | MKKIKKEAGKNILKLAPKEVAAKKSKKSPTK (SEQ ID NO:5) |
| synth-2a | 0 | 31 | 10.0 | 11.28 | PAAGESKVKANKKKAKILPTMKLKKEIKKKS (SEQ ID NO:6) |
| synth-2b | 0 | 31 | 10.0 | 11.28 | SEASLKAKIKKIAMKKVTKGKAKNKPKLPEK (SEQ ID NO:7) |
| synth-3: | | | | | |
| synth-3 | 0.92 | 63 | 3.0 | 10.41 | MKDKNSTGFLLSALLLAVTAGGSPVAAAPWNPFAAILKAALQIAGAAEPKEVTAKKGPTKADA (SEQ ID NO:8) |
| synth-3b | 0 | 63 | 3.0 | 10.41 | GWAGLVAETAIADKMSLKAAGEPPNQNDGAVLKTPPKAAASAKPLGAAKTLAFISPVTLALAK (SEQ ID NO:9) |
| synth-3c | 0 | 63 | 3.0 | 10.41 | AAKGVAAAFEANALSAWTTFMGLGGSIGFDKPPKKALKNKLTPAAVKSVLLPALATIAQEDAA (SEQ ID NO:10) | of the fraction of a sequence that is covered by identified patterns or grammars (FIG. 2B). In particular, FIG. 2A depicts a space diagram 20 that includes the sequence space 22 representative of the space that contains all possible sequences for a peptide of a particular length. The "sequence space" 22 is the combinatorially large set of all possible sequences. Even for a 20 amino acid peptide like synth-1 (see Table 1) this base is large: on the order of $10^{26}$ power of sequences. For comparison, that is a larger number than the number of stars in the known universe. It further depicts a grammar space 24 representative of the portion of possible The linguistic model employed in certain practices of the invention focuses the search base to the grammar space 24 but allows a deviation from natural peptide sequences. This allows the system 10 to be employed to design peptides that show no significant or virtually no significant homology to any naturally occurring sequences, but have the desired function. Homology in this context shall encompass the meaning of sequence similarity or identity, with identity being preferred. Identical in this context means, at least, identical amino acids at corresponding positions in the two sequences which are being compared. Homology may be understood to encompass a similarity or identity of sequence. Although, it may include optionally a measure of similarity that occurs when amino acids are identical or perhaps which are similar (functionally equivalent). The measure of homology employed by the processes described herein will vary according to the application at hand, and any appropriate measure of homology may be employed. Optionally, and typically, homology may be determined using standard techniques known in the art, such as the Best Fit sequence program described by Devereux, et al., Nucl. Acid Res., 12:387-395 (1984), or the BLASTX program (Altschul, et al., J. Mol. Biol., 215:403-410 (1990)).

FIG. 2B shows a subsequence of the synth-2 sequence. Above and below the subsequence are grammars that match the sequence in a tiled arrangement. For each bracketed expression any of the amino acids listed in the bracket will suffice. More specifically, FIG. 2B depicts a grammar 1 depicted as the sequence 30. The example grammar derived using the pattern recognition process discussed above includes a sequence of 10 amino acids. The grammar 1 has a number of optional expressions. For example, the second value of sequence may be either L or G. Similarly the third value of the sequence may be T, I or P. The first value of the sequence is T. Grammar 2, shown as sequence 38 is expressed using a similar notation.

As shown in FIG. 2B, both of the grammar sequences 30 and 38 are compared to the query sequence 32, and in this example, both are found within the sequence. As depicted, the grammar sequences 30 and 38 overlap each other. The result is that the query sequence has a score S 34 of 16/21. This score S indicates that grammars 30 and 38 cover sixteen of the twenty-one values in the query string. In the scoring process described and depicted in FIG. 2B, each grammar 30 and 38 is given equal weight. However, in optional practices, the grammars may be weighted or otherwise considered differently. For example, grammars that have been shown to be highly indicative of the characteristic of interest may be weighted more heavily than other sequences. This can tend to favor the survival of sequences having the more heavily weighted patterns. Alternatively, other patterns may by used to eliminate a sequence from further consideration, or evolution.

Moreover, in other embodiments, the systems and methods described herein allow for using a scoring function that considers two or more grammars generated from different and respective pattern recognition processes. For example, the scoring function may score a sequence based on the inclusion within the sequence of one or more patterns that are associated with a first characteristic, such as being antimicrobial, and the inclusion within the sequence of a pattern associated with a second characteristic, such as being anti-toxic. In this way, the processes described herein may have nested criteria to allow for the development of biological sequences that designed to exhibit two or more desirable characteristics.

To design synthetic AmPs, the described scoring process was employed to calculate the score S for a query sequence and to classify the query sequence as either grammatical or not. However, before designing sequences, we tested the ability of our linguistic model to distinguish between true AmP sequences and unrelated sequences. To this end, we used 90% of our AmP database to annotate the remaining 10% in the presence of non-AmP sequences from Swiss-Prot/TrEMBL. We randomly selected 90% of the known AmP sequences and generated a Teiresias grammar set. These grammars were used by our annotation software to identify the remaining 10% of our AmP database that was mixed with 10% of the non-AmP sequences from Swiss-Pro/TrEMBL (~78 K sequences). This experiment was repeated 300 times to determine the score S that maximized selectivity and sensitivity. We found that the score S=0.73 is optimal and that the model has a 99.95% sensitivity and a 99.95% selectivity.

Figure 3:
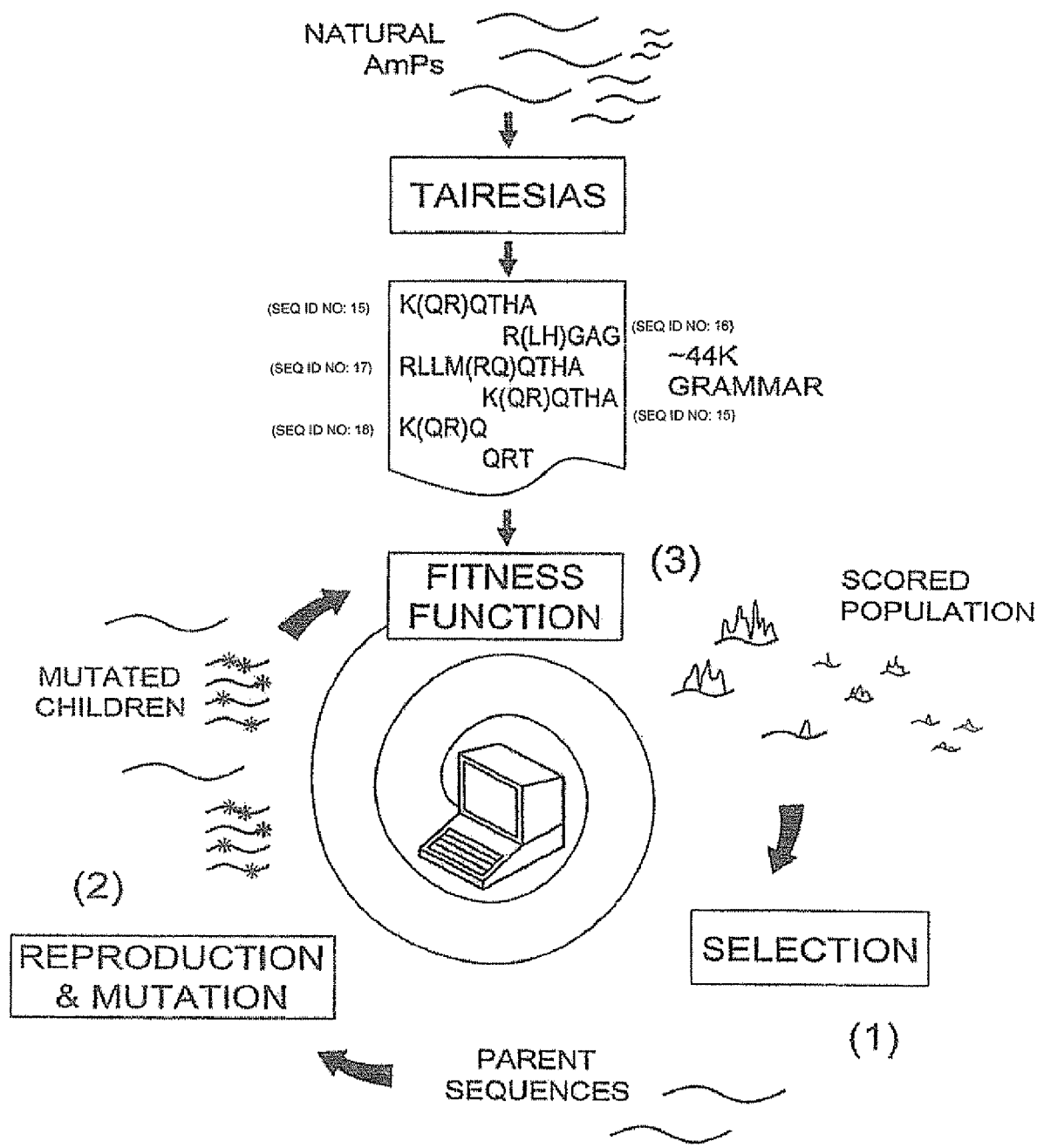
FIG. 3 depicts pictorially a schematic of the in silico directed evolutionary strategy employed by certain practices of the invention.

FIG. 3 depicts pictorially one process suitable for use with the systems and methods described herein. Specifically FIG. 3 depicts an evolution strategy and process 50 wherein in step 52 there is a starting point. The starting point may be a database of some number of paternal sequences. For example, the database may include 10,000; 100,000; 1,000,000, or more sequences. The sequences may be randomly generated and stored in the database to act as paternal sequences that will be reproduced and mutated. Each of these paternal sequences in step 52 may be processed in step 54 to be mutated and reproduced. For example, each of the sequences may have four mutated children as depicted in FIG. 3 wherein the mutations may be carried out using any suitable technique such as amino-acid substitution based on the blosum-50 matrix. This encourages, but does not require, the substitutions of similar amino acids. However, in other practices, the mutation process may be a fully random substitution process, or a probabilistic substitution process that assigns a probability of substitution to each residue and in the event a substitution does occur at that point in the sequence, the system will substitute based on a probabilistically determined substitution.

In either case, the mutated and reproduced children may be passed to a fitness function that is applied in step 58. The fitness function may be employed to score the entire population, generating a score S that may be associated with each of the child and parent sequences. The scoring, as described herein, employs the database of grammars generated from the natural antimicrobial peptides. From the scored population a set of candidate sequences, such as the top 100 sequences are chosen (based on the score for those sequences) and become the paternal sequences for the next iteration, or optionally set of iterations. In one such embodiment, the 100 most highly scored sequences are forwarded to step 54 to be reproduced and mutated. In one practice where four children were reproduced and mutated for each parent, the 100 sequences are turned into 500 mutated sequences. The parent and mutated children may be passed at the fitness function and again scored and again the top 100 most highly scored sequences may be kept. This iterative process may be continued until a set of candidate sequences is identified that have a score of sufficient interest to proceed with.

In one embodiment, a set number of cycles is established to run through the process 50. In one example, the process loop depicted in FIG. 3 was run 3,000 times. The first time with 100,000 sequences and the next 2,999 the cycles with the top 100 sequences as scored by the fitness function. Optionally and alternatively, the system 10 may be run by setting a threshold metric that identifies the score which is required for a certain number of sequences before the process will resolve itself. In either case, the system will generate a set of highly scored candidate sequences that may be considered for synthesis.

Figure 4:
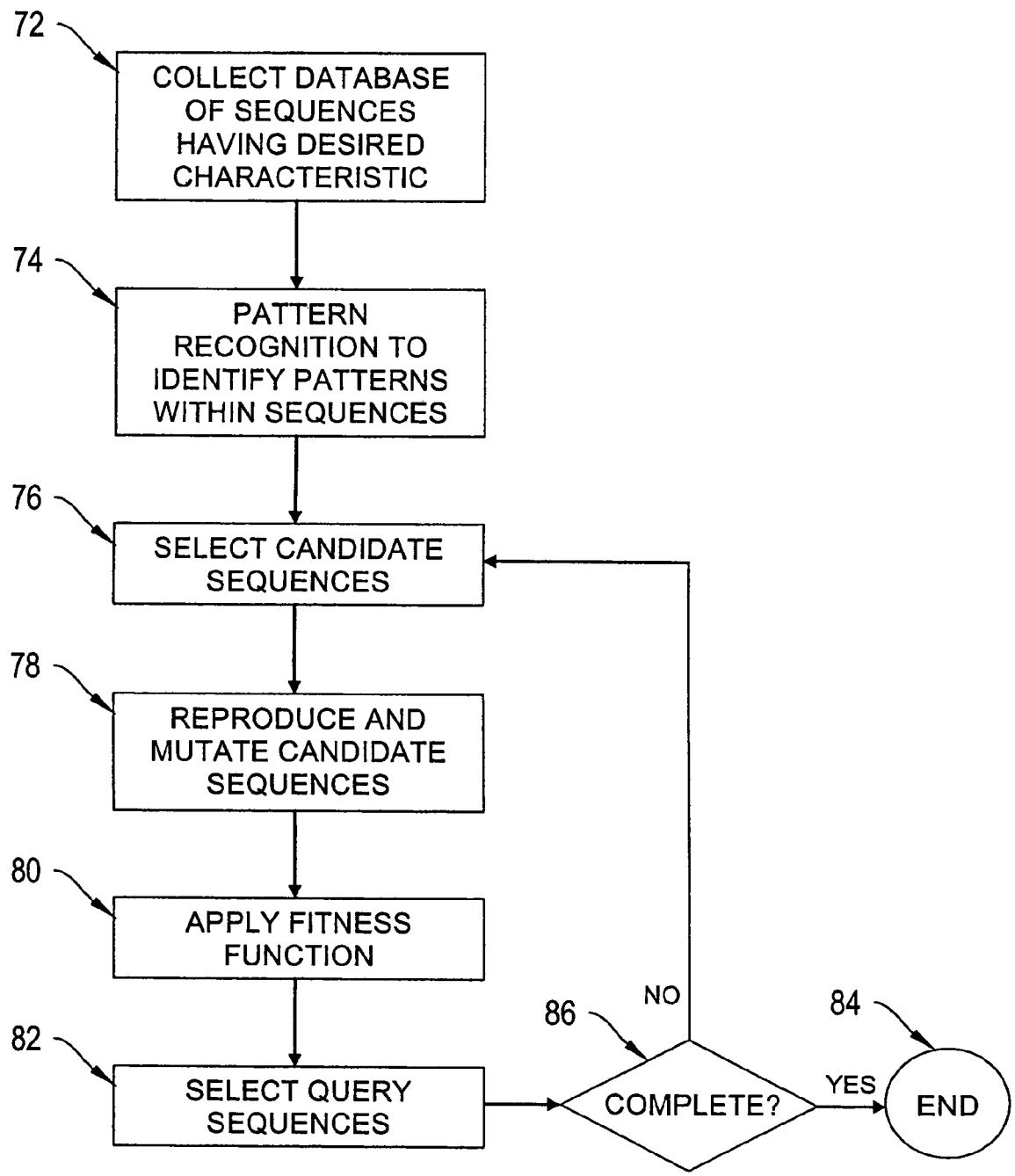
FIG. 4 depicts a flow chart diagram of one process for designing sequences according to the invention.

FIG. 4 depicts a flow chart diagram presenting in more detail the process shown pictorially in FIG. 3. More specifically, FIG. 4 depicts a flow chart of the type commonly employed to describe a computer program. The flow chart depicts a process 70 that begins in a step 72 wherein the process 70 collects a database of sequence data that has the characteristic of interest. As discussed above, the database may be a database of AmPs sequences that are naturally occurring. After step 72, the process 70 proceeds to step 74, where a pattern matching process is executed. Here the process 70 analyzes the sequence data to determine a set of expressions or a grammar for these sequences. In step 76, the process 70 will select candidate or query sequences. The selection step 76 may first comprise the random generation of a large number of query sequences. In one particular process, 500,000 query sequences are selected. This sequences may be generated by a sequence generator that randomly generates sequences to have a distribution with some diversity with regard to possible grammars. Once generated and selected, the process 70, in step 78 generates for each sequence, four children sequences that are mutated for each parent. Thus the 500,000 sequences are expanded into 2,000,000 sequences. The parent and mutated children may be passed at the fitness function in step 80 and scored by application of the fitness function. After step 80, the process proceeds to step 82, and tests at decision block 82 whether the process is complete. If not, the process returns to step 76, where the highest scoring sequences are selected and passed through the loop again. This iterative process may be continued until a set of candidate sequences is identified that have a score of sufficient interest to proceed with. At that point, in step 82, the process 70 may select the highest scoring sequences as the final sequences to consider for synthesis and testing.

In practice, three novel antimicrobial peptides were designed via in silico directed evolution using the described score S as a fitness function. To begin, as described above a database was created of 100 K progenitor sequences of uniform length with the same amino acid distribution as our AmP database. Each of these sequences was allowed to have four mutated children, which were each 100 PAM evolutionary units away from the parent (the implied rates of mutation from the Blosum-50 matrix were used to make the mutations at the amino acid level), S. Henikoff, J. G. Henikoff, *Proceedings of the National Academy of Sciences* 89, 10915 (1992). These children, each of which differed from their parent sequence by at least one amino acid, were added to the total population of sequences.

To avoid generating sequences that were similar to natural AmPs, the population was filtered (in an optional step) to purge any sequences that had six or more amino acids in common with any natural AmP sequence. The remaining sequences were scored using our annotation software. From the population, the sequences with the top 100 S-scores were propagated to the following round, and the entire process was repeated for 3,000 rounds.

Using the strategy described above, the process allowed many populations of various lengths to evolve, from which any number may be chosen to validate experimentally (sequences synth-1, 2, and 3 in Table 1). Each of these sequences is grammatical; however, none show significant homology to any naturally occurring protein (NBCI Blast, S. Altschul, et al. *Nucleic Acids Research* 25, 3389 (1997), default parameters using NR database). This is possible because each grammar can be written in a large number of ways. For example, the 10 residue grammar [LV] [GA] [TN] [FL] AGHML (SEQ ID NO: 14) occurs in 3 natural AmPs, but there are 16 possible 10-aa sequences that match this grammar. Since these sequences are built from tiled grammars, the synthetic sequences can quickly deviate from the naturally populated sequence space such that it is impossible to detect similarity using sequence alignment tools.

These synthetic sequences may be validated experimentally, along with a set of shuffled sequence controls (all peptides are shown in Table 1). Each peptide may be synthesized.

In a preferred embodiment, the designed proteins are chemically synthesized as is known in the art. Laboratory synthesis of peptides has risen to the level of a well-defined art in recent years. Synthetic peptides, composed of as many as a hundred amino acids in specified sequence, have been prepared in the laboratory with good purity and high yields. In organic chemistry, peptide synthesis is the creation of peptides, which are organic compounds in which more than two amino acids bind via peptide bonds. Peptides are synthesized by combining the carboxyl group of one amino acid with the amino group of another. During peptide synthesis, one side of the amino acids has to be protected to keep the acids from reacting with themselves. There are two conventional types of methods for obtaining polypeptides. One is the stepwise elongation method, in which the amino acids are connected step-by-step in turn. The other is the fragment condensation method, in which peptide fragments are coupled to each other. Although the former can elongate the peptide chain without racemization, the yield drops if only it is used. Fragment condensation is better than stepwise elongation for synthesizing sophisticated long peptides, but its use must be restricted in order to protect the racemization. There are two conventional ways of synthesizing polypeptides. One is liquid-phase peptide synthesis, and the other is solid-phase peptide synthesis. When the former is utilized, the product can usually be purified halfway, yet time, effort, skill, and experience are necessary. When the latter is used, less time and effort are necessary for the synthesis because the experimental operation is simpler, but it is impossible to purify the peptide during the process.

The choice of which method to use is left to the person who synthesizes the peptide. The established practices for peptide synthesis are particularly useful when the designed proteins are short, preferably less than 150 amino acids in length, with less than 100 amino acids being preferred, and less than 50 amino acids being particularly preferred, although as is known in the art, longer proteins can be made chemically or enzymatically.

In an optional practice, particularly for longer proteins or proteins for which large samples are desired, the optimized sequence is used to create a nucleic acid such as DNA which encodes the optimized sequence and which can then be cloned into a host cell and expressed. Thus, nucleic acids, and particularly DNA, can be made which encodes each optimized protein sequence. This is done using well known procedures. The choice of codons, suitable expression vectors and suitable host cells will vary depending on a number of factors, and can be easily optimized as needed.

Once made, the designed proteins and peptides may be experimentally evaluated and tested for structure, function and stability, as required. This will be done as is known in the art.

The activity of each AmP can be studied against a number of bacterial species: *E. coli, C. rodentium, B. subtilis,* and *C. glutamicum.* to determine the presence of antimicrobial activity for these peptides as compared to the control sequences.

The antimicrobial assays may be based on the NCCLS protocol M26-A, and a close variation on that, the method of RW Hancock for Cationic peptides. Cells may be grown overnight in Mueller Hinton Broth (MHB) or Cation adjusted MHB. These cells may be diluted in fresh MHB to an initial concentration of around $5*10^5$ cfu/ml.

Serial 2 fold dilutions of the antimicrobial are made at 10-fold the desired concentration in sterile water. In the Hancock variation 0.2% BSA and 0.01% Acetic Acid are used rather than water. 11 ul of antimicrobial are added to 100 ul of the inoculum at $5*10^5$ cfu/ml and grown overnight. The MIC is the first concentration of peptide that prohibits growth as measured by OD at 24 hours. The MBC can be found by performing plate counting on the sample that do not have a measurable OD.

Previous approaches to the design of synthetic AmPs have produced peptides that are either closely related to naturally occurring peptides, or that are composed of only a handful of amino acids, for example, poly-lysine peptides, E. Tiozzo, G. Rocco, A. Tossi, D. Romeo, *Biochemical and Biophysical Research Communications* 249, 202 (1998), A. Tossi, L. Sandri, A. Giangaspero, *Biopolymers* 55, 4 (2000). In contrast, our synthetic AmPs, by design, have an amino acid distribution similar to that of natural proteins and they populate a region of sequence space that is not occupied by naturally occurring AmPs. In essence, our linguistic approach is a means to rationally expand the natural sequence space without using structure-activity information or complex folding simulations. Instead, we rely upon the ability of sequence grammars to capture the underlying functions of the peptides. These grammars help to establish bounds on the set of synthetic sequences that are likely to have antimicrobial activity.

We expect that linguistic strategies, like the grammar-based approach used here, could lead to the design of many AmPs. As the annotation of both known and synthetic AmPs becomes more complete, the processes herein will make it possible to build custom-made peptides with targeted activities using similar approaches.

The methods described above may be extended to generate, a much larger number of candidate sequences. For example, by increasing the size of the random sequence list originally generated, such as from a 100,000 to 1,000,000, it may be expected that the number of highly scored candidate sequences may be increased from a few hundred to a few thousand. The few thousand candidate sequences may be tested against a series of different bacteria to determine which ones are effective. Additionally, the systems and methods described herein may be employed to generate peptides that have multiple desired characteristics. For example, the systems and methods described herein may be extended to take into consideration a second or third characteristics, such as the hemolytic characteristic of a peptide. To this end, and as described above patterns—such as grammars—may be generated or peptides having these second and third characteristics. Of the candidate sequences generated, the systems and methods described herein may apply these new patterns to the candidate sequences to identify sequences that meet both criteria, and therefore provide both properties.

The proteins and peptides processed and designed by the systems and methods described herein may be for any organism, including prokaryotes and eukaryotes, with enzymes from bacteria, fungi, extremeophiles such as the archebacteria, insects, fish, animals (particularly mammals and particularly human) and birds all possible. Suitable proteins include, but are not limited to, industrial and pharmaceutical proteins, including ligands, cell surface receptors, antigens, antibodies, cytokines, hormones, and enzymes. Suitable classes of enzymes include, but are not limited to, hydrolases such as proteases, carbohydrases, lipases; isomerases such as racemases, epimerases, tautomerases, or mutases; transferases, kinases, oxidoreductases, and phophatases. Suitable enzymes are listed in the Swiss-Prot enzyme database.

Specifically included within "protein" are fragments and domains of known proteins, including functional domains such as enzymatic domains, binding domains, etc., and smaller fragments, such as turns, loops, etc. That is, portions of proteins may be used as well.

Moreover, the proteins may be designed to have additional features and characteristics. For example, they may be more stable than the known peptides that were used as the starting point. Stable may mean that the new protein retains either biological activity or conformation past the point at which the parent molecule did. Stability includes, but is not limited to, thermal stability, i.e. an increase in the temperature at which reversible or irreversible denaturing starts to occur; proteolytic stability, i.e. a decrease in the amount of protein which is irreversibly cleaved in the presence of a particular protease (including autolysis); stability to alterations in pH or oxidative conditions; chelator stability; stability to metal ions; stability to solvents such as organic solvents, surfactants, formulation chemicals; etc.

Once made, the proteins of the invention find use in a wide variety of applications, as will be appreciated by those in the art, ranging from industrial to pharmacological uses, depending on the protein. Thus, for example, proteins and enzymes exhibiting increased thermal stability may be used in industrial processes that are frequently run at elevated temperatures, for example carbohydrate processing (including saccharification and liquifaction of starch to produce high fructose corn syrup and other sweeteners), protein processing (for example the use of proteases in laundry detergents, food processing, feed stock processing, baking, etc.), etc. Similarly, the methods of the present invention allow the generation of useful pharmaceutical proteins, such as analogs of known proteinaceous drugs.

The pattern detection systems and the described evolutionary candidate peptide production processes described above may be realized as software processes that were designed and developed following from principles known in the art of computer programming, including those set forth in Wall et al., *Programming Perl*, O'Reilly & Associates (1996); and Johnson et al, *Linux Application Development*, Addison-Wesley (1998). FIG. 2 further depicts the process as including a server. The server may be a conventional data processing platform such as an IBM PC-compatible computer running the Windows operating systems, or a SUN workstation running a Unix operating system. Alternatively, the data processing system can comprise a dedicated processing system that includes an embedded programmable data processing system. For example, the data processing system can comprise a single board computer system that has been integrated into a system for performing peptide design process. As discussed above, the peptide design systems can be realized as a software component operating on a conventional data processing system such as a Unix workstation. In that embodiment, the peptide design system can be implemented as a C language computer program, or a computer program written in any high level language including C++, Fortran, Java or basic. Additionally, in an embodiment where microcontrollers or DSPs are employed, the peptide design system can be realized as a computer program written in microcode or written in a high level language and compiled down to microcode that can be executed on the platform employed. The development of such peptide design system is known to those of skill in the art, and such techniques are set forth in Digital Signal Processing Applications with the TMS320 Family, Volumes I, II, and III, Texas Instruments (1990). Additionally, general techniques for high level programming are known, and set forth in, for example, Stephen G. Kochan, *Programming in C*, Hayden Publishing (1983). It is noted that DSPs are particularly suited for implementing signal processing functions, including preprocessing functions such as image enhancement through adjustments in contrast, edge definition and brightness. Developing code for the DSP and microcontroller systems follows from principles well known in the art.

The discussed databases can be any suitable database system, including the commercially available Microsoft Access database, and can be a local or distributed database system. The design and development of suitable database systems are described in McGovern et al., *A Guide To Sybase and SQL Server*, Addison-Wesley (1993). The database can be supported by any suitable persistent data memory, such as a hard disk drive, RAID system, tape drive system, floppy diskette, or any other suitable system.

Those skilled in the art will know or be able to ascertain using no more than routine experimentation, many equivalents to the embodiments and practices described herein. Accordingly, it will be understood that the invention is not to be limited to the embodiments disclosed herein, but is to be understood from the following claims, which are to be interpreted as broadly as allowed under the law.

What is claimed is:

1. A method for making an antimicrobial peptide, comprising the steps of
determining a set of patterns of primary amino acid sequences being representative of a peptide having antimicrobial activity in a database of antimicrobial peptides selected from the group consisting of AMSDb and SWISS-PROT,
providing a set of randomly generated peptide sequences at least ten amino acids in length,
correlating the set of patterns with the randomly generated peptide sequences by calculating the S score,
selecting at least one of said randomly generated peptide sequences having a score $S=16/21$ or 0.73 or higher and mutating the selected peptide sequence,
repeating the step of correlating the set of patterns with the mutated peptide sequences to identify mutated peptide sequences having a score $S=16/21$ or 0.73 or higher scored peptide sequences,
selecting an identified peptide sequence, and
synthesizing the peptide sequence.

2. A method according to claim 1, wherein correlating the set of patterns with the randomly generated sequences includes processing a sequence to determine a score representative of a percentage of the sequence that matches to a pattern in the set of patterns, wherein the percentage is 90%.

3. A method according to claim 1, wherein mutating a sequence includes a substitution process wherein substitution among similar entities is preferred.

4. A method according to claim 1, wherein determining a set of patterns includes identifying a set of patterns in a data set of biological sequences having antimicrobial activity.

5. A method according to claim 4, further comprising identifying a database of biological sequence data wherein the biological sequence data is representative of naturally occurring antimicrobial peptides.

6. A method according to claim 4, wherein identifying a set of patterns includes identifying a substantially exhaustive set of patterns from the database of biological sequences.

7. A method according to claim 1, further comprising determining a second set of patterns being representative of a peptide having a second characteristic of interest, and correlating the mutated peptide sequences with the second set of patterns to identify peptide sequences having the first characteristic and the second characteristic of interest.

8. The method of claim 7, wherein the second characteristic of interest is selected from the group consisting of anti-viral, a selected topography, hydrophobic, hydrophilic, and thermally stable.

9. The method of claim 1, further comprising comparing the mutated peptide with a sequence representative of a naturally occurring peptide and determining a degree of homology.

10. The method according to claim 9, further comprising removing a mutated peptide having a degree of homology greater than a selected maximum.

11. The method of claim 1, including the further step of synthesizing a peptide having substantially the selected mutated peptide sequence.

12. The method of claim 11 including the further step of testing activity of a synthesized peptide for antimicrobial activity.

* * * * *

UNITED STATES PATENT AND TRADEMARK OFFICE
CERTIFICATE OF CORRECTION

PATENT NO.      : 7,603,239 B2                                    Page 1 of 1
APPLICATION NO. : 11/123399
DATED           : October 13, 2009
INVENTOR(S)     : Stephanopoulos et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 62 days.

Signed and Sealed this

Fifth Day of October, 2010

David J. Kappos
*Director of the United States Patent and Trademark Office*

```
                              SEQUENCE LISTING

<160> NUMBER OF SEQ ID NOS: 13

<210> SEQ ID NO 1
   <211> LENGTH: 12
   <212> TYPE: PRT
   <213> ORGANISM: Artificial Sequence
   <220> FEATURE:
   <223> OTHER INFORMATION: chemically synthesized
   <220> FEATURE:
   <221> NAME/KEY: VARIANT
   <222> LOCATION: 2, 6, 8, 10, 11
   <223> OTHER INFORMATION: Xaa = Any Amino Acid

<400> SEQUENCE: 1

Gln Xaa Glu Ala Gly Xaa Leu Xaa Lys Xaa Xaa Lys
   1               5                   10

<210> SEQ ID NO 2
   <211> LENGTH: 20
   <212> TYPE: PRT
   <213> ORGANISM: Artificial Sequence
   <220> FEATURE:
   <223> OTHER INFORMATION: chemically synthesized

<400> SEQUENCE: 2

Asn Lys Val Lys Lys Pro Leu Thr Gly Ala His Arg Leu Leu Phe Thr
   1               5                   10                  15

Phe Leu Phe Val
               20

<210> SEQ ID NO 3
   <211> LENGTH: 20
   <212> TYPE: PRT
   <213> ORGANISM: Artificial Sequence
   <220> FEATURE:
   <223> OTHER INFORMATION: chemically synthesized

<400> SEQUENCE: 3

Val Val Leu Lys Leu Leu Phe Phe Lys Phe Asn Leu Pro His Lys Thr
   1               5                   10                  15

Arg Thr Ala Gly
               20

<210> SEQ ID NO 4
   <211> LENGTH: 20
   <212> TYPE: PRT
   <213> ORGANISM: Artificial Sequence
   <220> FEATURE:
   <223> OTHER INFORMATION: chemically synthesized

<400> SEQUENCE: 4

Leu Val Leu Thr Phe Leu Phe Ala Thr Pro Lys Leu Asn Gly Arg Val
   1               5                   10                  15

Lys Lys Phe His
               20

<210> SEQ ID NO 5
   <211> LENGTH: 31
```

```
<212> TYPE: PRT
<213> ORGANISM: Artificial Sequence
<220> FEATURE:
<223> OTHER INFORMATION: chemically synthesized

<400> SEQUENCE: 5

Met Lys Lys Ile Lys Lys Glu Ala Gly Lys Asn Ile Leu Lys Leu Ala
1               5                   10                  15

Pro Lys Glu Val Ala Ala Lys Ser Lys Lys Ser Pro Thr Lys
            20                  25                  30

<210> SEQ ID NO 6
<211> LENGTH: 31
<212> TYPE: PRT
<213> ORGANISM: Artificial Sequence
<220> FEATURE:
<223> OTHER INFORMATION: chemically synthesized

<400> SEQUENCE: 6

Pro Ala Ala Gly Glu Ser Lys Val Lys Ala Asn Lys Lys Ala Lys
1               5                   10                  15

Ile Leu Pro Thr Met Lys Leu Lys Lys Glu Ile Lys Lys Lys Ser
            20                  25                  30

<210> SEQ ID NO 7
<211> LENGTH: 31
<212> TYPE: PRT
<213> ORGANISM: Artificial Sequence
<220> FEATURE:
<223> OTHER INFORMATION: chemically synthesized

<400> SEQUENCE: 7

Ser Glu Ala Ser Leu Lys Ala Lys Ile Lys Lys Ile Ala Met Lys Lys
1               5                   10                  15

Val Thr Lys Gly Lys Ala Lys Asn Lys Pro Lys Leu Pro Glu Lys
            20                  25                  30

<210> SEQ ID NO 8
<211> LENGTH: 63
<212> TYPE: PRT
<213> ORGANISM: Artificial Sequence
<220> FEATURE:
<223> OTHER INFORMATION: chemically synthesized

<400> SEQUENCE: 8

Met Lys Asp Lys Asn Ser Thr Gly Pro Leu Leu Ser Ala Leu Leu Leu
1               5                   10                  15

Ala Val Thr Ala Gly Gly Ser Pro Val Ala Ala Ala Pro Trp Asn Pro
            20                  25                  30

Phe Ala Ala Ile Leu Lys Ala Ala Leu Gln Ile Ala Gly Ala Ala Glu
                35                  40                  45

Pro Lys Glu Val Thr Ala Lys Lys Gly Pro Thr Lys Ala Asp Ala
            50                  55                  60

<210> SEQ ID NO 9
<211> LENGTH: 63
<212> TYPE: PRT
<213> ORGANISM: Artificial Sequence
<220> FEATURE:
<223> OTHER INFORMATION: chemically synthesized

<400> SEQUENCE: 9

Gly Trp Ala Gly Leu Val Ala Glu Thr Ala Ile Ala Asp Lys Met Ser
1               5                   10                  15
```

Leu Lys Ala Ala Gly Glu Pro Pro Asn Gln Asn Asp Gly Ala Val Leu
        20                  25                  30

Lys Thr Pro Pro Lys Ala Ala Ser Ala Lys Pro Leu Gly Ala Ala
        35                  40                  45

Lys Thr Leu Ala Phe Ile Ser Pro Val Thr Leu Ala Leu Ala Lys
        50                  55                  60

<210> SEQ ID NO 10
<211> LENGTH: 63
<212> TYPE: PRT
<213> ORGANISM: Artificial Sequence
<220> FEATURE:
<223> OTHER INFORMATION: chemically synthesized

<400> SEQUENCE: 10

Ala Ala Lys Gly Val Ala Ala Ala Pro Glu Ala Asn Ala Leu Ser Ala
  1               5                  10                  15

Trp Thr Thr Pro Met Gly Leu Gly Gly Ser Ile Gly Phe Asp Lys Pro
        20                  25                  30

Pro Lys Lys Ala Leu Lys Asn Lys Leu Thr Pro Ala Ala Val Lys Ser
        35                  40                  45

Val Leu Leu Pro Ala Leu Ala Thr Ile Ala Gln Glu Asp Ala Ala
        50                  55                  60

<210> SEQ ID NO 11
<211> LENGTH: 10
<212> TYPE: PRT
<213> ORGANISM: Artificial Sequence
<220> FEATURE:
<223> OTHER INFORMATION: chemically synthesized
<220> FEATURE:
<221> NAME/KEY: VARIANT
<222> LOCATION: 2
<223> OTHER INFORMATION: Xaa = Leu or Gly
<220> FEATURE:
<221> NAME/KEY: VARIANT
<222> LOCATION: 3
<223> OTHER INFORMATION: Xaa = Thr, Ile or Pro
<220> FEATURE:
<221> NAME/KEY: VARIANT
<222> LOCATION: 6
<223> OTHER INFORMATION: Xaa = Thr, Ile, Ser or Pro
<220> FEATURE:
<221> NAME/KEY: VARIANT
<222> LOCATION: 7
<223> OTHER INFORMATION: Xaa = Ala or Thr
<220> FEATURE:
<221> NAME/KEY: VARIANT
<222> LOCATION: 10
<223> OTHER INFORMATION: Xaa = Leu or Gly

<400> SEQUENCE: 11

Thr Xaa Xaa Leu Leu Xaa Xaa Leu Leu Xaa
  1               5                  10

<210> SEQ ID NO 12
<211> LENGTH: 21
<212> TYPE: PRT
<213> ORGANISM: Artificial Sequence
<220> FEATURE:
<223> OTHER INFORMATION: chemically synthesized

<400> SEQUENCE: 12

Met Lys Ser Thr Gly Pro Leu Leu Ser Ala Leu Leu Leu Ala Val Thr
  1               5                  10                  15

Ala Gly Gly Asp Pro

```
                                    20

<210> SEQ ID NO 13
<211> LENGTH: 10
<212> TYPE: PRT
<213> ORGANISM: Artificial Sequence
<220> FEATURE:
<223> OTHER INFORMATION: chemically synthesized
<220> FEATURE:
<221> NAME/KEY: VARIANT
<222> LOCATION: 1
<223> OTHER INFORMATION: Xaa = Ala, Phe or Thr
<220> FEATURE:
<221> NAME/KEY: VARIANT
<222> LOCATION: 3
<223> OTHER INFORMATION: Xaa = Ile or Leu
<220> FEATURE:
<221> NAME/KEY: VARIANT
<222> LOCATION: 6
<223> OTHER INFORMATION: Xaa = Ile or Val
<220> FEATURE:
<221> NAME/KEY: VARIANT
<222> LOCATION: 7
<223> OTHER INFORMATION: Xaa = Ser, Phe, Ala or Thr
<220> FEATURE:
<221> NAME/KEY: VARIANT
<222> LOCATION: 8
<223> OTHER INFORMATION: Xaa = Val or Ala
<220> FEATURE:
<221> NAME/KEY: VARIANT
<222> LOCATION: (9)...(9)
<223> OTHER INFORMATION: Xaa = Gly, Ala or Asp
<220> FEATURE:
<221> NAME/KEY: VARIANT
<222> LOCATION: (10)...(10)
<223> OTHER INFORMATION: Xaa = Pro, Gly, Ser or Gln

<400> SEQUENCE: 13

Xaa Leu Xaa Leu Ala Xaa Xaa Xaa Xaa Xaa
 1               5                  10
```